US009466093B2

(12) United States Patent
Geiger

(10) Patent No.: US 9,466,093 B2
(45) Date of Patent: Oct. 11, 2016

(54) ANTERIOR COMMISSURE AND POSTERIOR COMMISSURE SEGMENTATION SYSTEM AND METHOD

(71) Applicant: Cedara Software Corp., Mississauga (CA)

(72) Inventor: Paul Arthur Geiger, Toronto (CA)

(73) Assignee: Cedara Software Corp., Mississauga, Ontario (CA)

( * ) Notice: Subject to any disclaimer, the term of this patent is extended or adjusted under 35 U.S.C. 154(b) by 198 days.

(21) Appl. No.: 14/264,817

(22) Filed: Apr. 29, 2014

(65) Prior Publication Data

US 2014/0233824 A1  Aug. 21, 2014

Related U.S. Application Data

(63) Continuation of application No. 13/618,551, filed on Sep. 14, 2012, now Pat. No. 8,737,712, which is a continuation of application No. 12/420,660, filed on Apr. 8, 2009, now Pat. No. 8,270,698, which is a continuation-in-part of application No. 12/236,854, filed on Sep. 24, 2008, now Pat. No. 8,315,689.

(51) Int. Cl.
*G06K 9/00* (2006.01)
*G06T 3/00* (2006.01)

(52) U.S. Cl.
CPC .................................. *G06T 3/0031* (2013.01)

(58) Field of Classification Search
None
See application file for complete search history.

(56) References Cited

U.S. PATENT DOCUMENTS

| | | |
|---|---|---|
| 7,167,760 B2 | 1/2007 | Dawant et al. |
| 7,357,934 B2 | 4/2008 | Donovan et al. |
| 7,409,085 B2 | 8/2008 | Hu et al. |
| 7,756,306 B2 | 7/2010 | Nowinski et al. |
| 8,019,142 B2 | 9/2011 | Nowinski et al. |

(Continued)

FOREIGN PATENT DOCUMENTS

| | | |
|---|---|---|
| WO | 03060827 | 7/2003 |
| WO | 2006118549 | 11/2006 |

OTHER PUBLICATIONS

G. Ruppert, L. Teverovskiy, C. Yu, A Falcao, and Y. Liu. A new symmetry-based method for mid-sagittal plane extraction in neuroimages. In IEEE International Symposium on Biomedical Imaging: From Nano to Macro, pp. 285-288, Chicago, 2011.*

(Continued)

*Primary Examiner* — Shefali Goradia
(74) *Attorney, Agent, or Firm* — Michael Best & Friedrich LLP

(57) ABSTRACT

A computer-implemented system and method of determining anterior commissure (AC) and posterior commissure (PC) points in a volumetric neuroradiological image. The method includes determining, by a computer, a mid-sagittal plane estimate to extract a mid-sagittal plane image from the volumetric neuroradiological image, and AC and PC point estimates in the mid-sagittal plane image. The method further includes determining, by the computer, a refined mid-sagittal plane estimate from the AC and PC point estimates to extract a refined mid-sagittal plane image, the AC point from the refined mid-sagittal plane image, and the PC point from the refined mid-sagittal plane image and the AC point.

20 Claims, 15 Drawing Sheets

(56) References Cited

U.S. PATENT DOCUMENTS

| | | | |
|---|---|---|---|
| 8,045,775 B2 | 10/2011 | Volkau et al. | |
| 8,270,698 B2 | 9/2012 | Geiger | |
| 8,442,288 B2 * | 5/2013 | Luisi | G06T 17/30 345/420 |
| 8,737,712 B2 | 5/2014 | Geiger | |
| 2006/0058855 A1 | 3/2006 | Gill | |
| 2007/0076927 A1 | 4/2007 | Nagaraja Rao et al. | |
| 2008/0123923 A1 | 5/2008 | Gielen et al. | |
| 2009/0128553 A1 | 5/2009 | Perry et al. | |

OTHER PUBLICATIONS

Yanxi Liu and Robert Collins, "Automatic Extraction of the Central Symmetry Plane from Neuroradiology Images," tech. report CMU-RI-TR-96-40, Robotics Institute, Carnegie Mellon University, Dec. 1996.*

PCT/CA2009/000444 International Search Report and Written Opinion of the International Searching Authority mailed Aug. 12, 2009, 9 pages.

Liu, Yanxi, et al., "Robust Midsagittal Plane Extraction from Normal and Pathological 3-D Neuroradiology Images," IEEE Transactions on Medical Imaging, vol. 20, No. 3, Mar. 2001, pp. 175-192.

Han et al., "Automatic Brain MR Image Registration Based on Talairach Reference System," Image processing, ICIP 2003, Sep. 14-17, 2003, vol. 1, pp. 1097-1100.

Office Action from the United States Patent and Trademark Office for U.S. Appl. No. 12/420,660 dated Apr. 2, 2012, 10 pages.

Weiss, "Clinical Brain MR Imaging Prescriptions in Talairach Space: Technologist-and Computer-Driven Methods," AJNR, American Journal of Neurology, Jan. 1, 2003, vol. 24, pp. 994-929.

Bhanu Prakash, et al., "Rapid and Automatic Localization of the Anterior and Posterior Commissure Point Landmarks in MR Volumetric Neuroimages," Academic Radiology, Jan. 1, 2006, vol. 13, No. 1, pp. 36-54.

Nowinski, et al., "Fast Talairach Transformation for Magnetic Resonance Neuroimages," Journal of Computer Assisted Tomography, Jul. 1, 2006, vol. 30, No. 4 pp. 629-641.

Search Report from the European Patent Office for Application No. 09815511 dated Sep. 11, 2012, 5 pages.

Office Action from the Canadian Intellectual Property Office for Application No. 2748053 dated Oct. 14, 2015 (4 pages).

* cited by examiner

ANTERIOR COMMISSURE AND POSTERIOR COMMISSURE SEGMENTATION SYSTEM AND METHOD

CROSS-REFERENCE TO RELATED APPLICATIONS

This application is a continuation of U.S. patent application Ser. No. 13/618,551, filed Sep. 14, 2012, which is a continuation of U.S. patent application Ser. No. 12/420,660, filed Apr. 8, 2009, now U.S. Pat. No. 8,270,698, which is a continuation-in-part of U.S. patent application Ser. No. 12/236,854, filed Sep. 24, 2008, now U.S. Pat. No. 8,315,689, the entire contents of which are each hereby incorporated by reference.

BACKGROUND

The present invention relates to a system and method for locating the anterior and posterior commissures (AC and PC) in a three-dimensional image of a human brain. Identification of the AC and PC are critical for operations such as targeting stereotactic and functional neurosurgery, localization, analysis in brain mapping, structure segmentation and labeling neuroradiology. For example, the Talairach atlas and its associated transformations, which have been widely used as a standard by neuroscientists and neurosurgeons to perform spatial normalization, require identification of the mid-sagittal plane (MSP), AC and PC.

Manual identification of the AC and PC from a volumetric neuroradiological image is tedious and inherently results in a degree of variability across analysts, while identification of these structures by known computer image analysis methods is either too computationally time-consuming or produces unreliable results. For these reasons, there is a need for an automated method of AC and PC identification that is simultaneously accurate, robust, and efficient.

SUMMARY

In one embodiment, the invention provides a computer-implemented method of determining anterior commissure (AC) and posterior commissure (PC) points in a volumetric neuroradiological image. The method includes determining, by a computer, a mid-sagittal plane estimate to extract a mid-sagittal plane image from the volumetric neuroradiological image, and AC and PC point estimates in the mid-sagittal plane image. The method further includes determining, by the computer, a refined mid-sagittal plane estimate from the AC and PC point estimates to extract a refined mid-sagittal plane image, the AC point from the refined mid-sagittal sagittal plane image, and the PC point from the refined mid-sagittal plane image and the AC point.

In another embodiment, the invention provides a computer readable medium encoded with a plurality of processor executable instructions for identifying AC and PC points in a volumetric neuroradiological image, the instructions enabling execution of the method outlined above.

In still another embodiment, the invention provides an image processing system configured to determine AC and PC points in a volumetric neuroradiological image. The system includes a first estimator to determine a mid-sagittal plane approximation from the volumetric neuroradiological image, and a second estimator to determine AC and PC point approximations from the mid-sagittal plane approximation. The system also includes a first refining module to identify a mid-sagittal plane using the AC and PC point approximations, a second refining module to identify the AC point from the mid-sagittal plane, and a third refining module to identify the PC point from the mid-sagittal plane and the AC point.

Other aspects of the invention will become apparent by consideration of the detailed description and accompanying drawings.

DETAILED DESCRIPTION

Before any embodiments of the invention are explained in detail, it is to be understood that the invention is not limited in its application to the details of the method steps and the parameters of individual algorithms set forth in the following description or illustrated in the following drawings. The invention is capable of other embodiments and of being practiced or of being carried out in various ways.

The system and method of the present invention are broadly applicable to input volumetric image data obtained via magnetic resonance imaging (MR and fMR) and computed tomography (CT), and can be implemented with data from other imaging modalities, given an appropriate degree of resolution and contrast. Further, data from multiple modalities can be merged to create a hybrid data set with which the system and method can be implemented. The input image data can be obtained directly from an imaging modality or picture archiving and communications system (PACS), or from a database accessible via the internet.

In an embodiment of the invention, the AC-PC segmentation method is broken down into the following five basic phases: 1) approximation of the mid-sagittal plane (MSP), 2)

approximation of the AC and PC points, 3) refining the mid-sagittal plane, 4) refining the AC point, and 5) refining the PC point. These phases (and the steps within each phase identified and discussed in detail below) are only defined as such for the purposes of explanation. Thus, it should be understood by one of ordinary skill in the art that combination of consecutive phases/steps and/or separate execution of elements of individual steps are within the scope of the invention. Further, all the steps identified below are not required in all embodiments of the invention, and some variance from the order of the steps within the process as described below is also within the scope of the invention.

Figure 1:
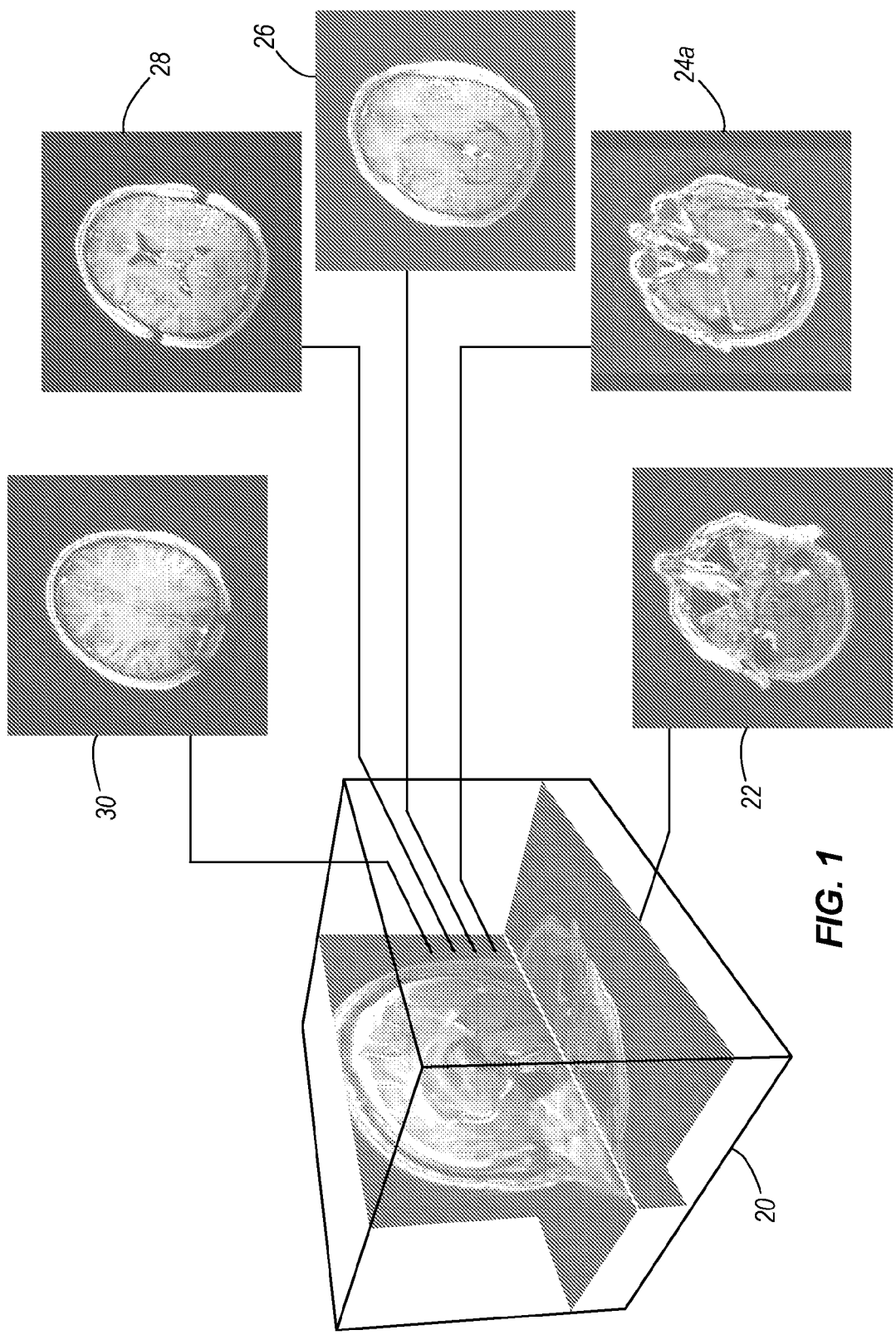
FIG. 1 includes a series of axial image slices taken from a volumetric scan of a human head.

The first phase, approximation of the mid-sagittal plane from a volumetric image, begins by extracting several two-dimensional axial images, or slices, from the image volume 20. As shown in FIG. 1, the selected slices 22, 24a, 26, 28, 30 approximately span the vertical (axial) range from the medulla to the top of the corpus calossum. Outside of this range, the cross-sectional images of the head and neck tend to be roughly circular; hence, they are not as useful for determining the orientation of the head by this method. In some embodiments, about 15 equally-spaced images can be used, but the exact number is not critical, nor is the requirement that they be equally spaced.

Figure 2:
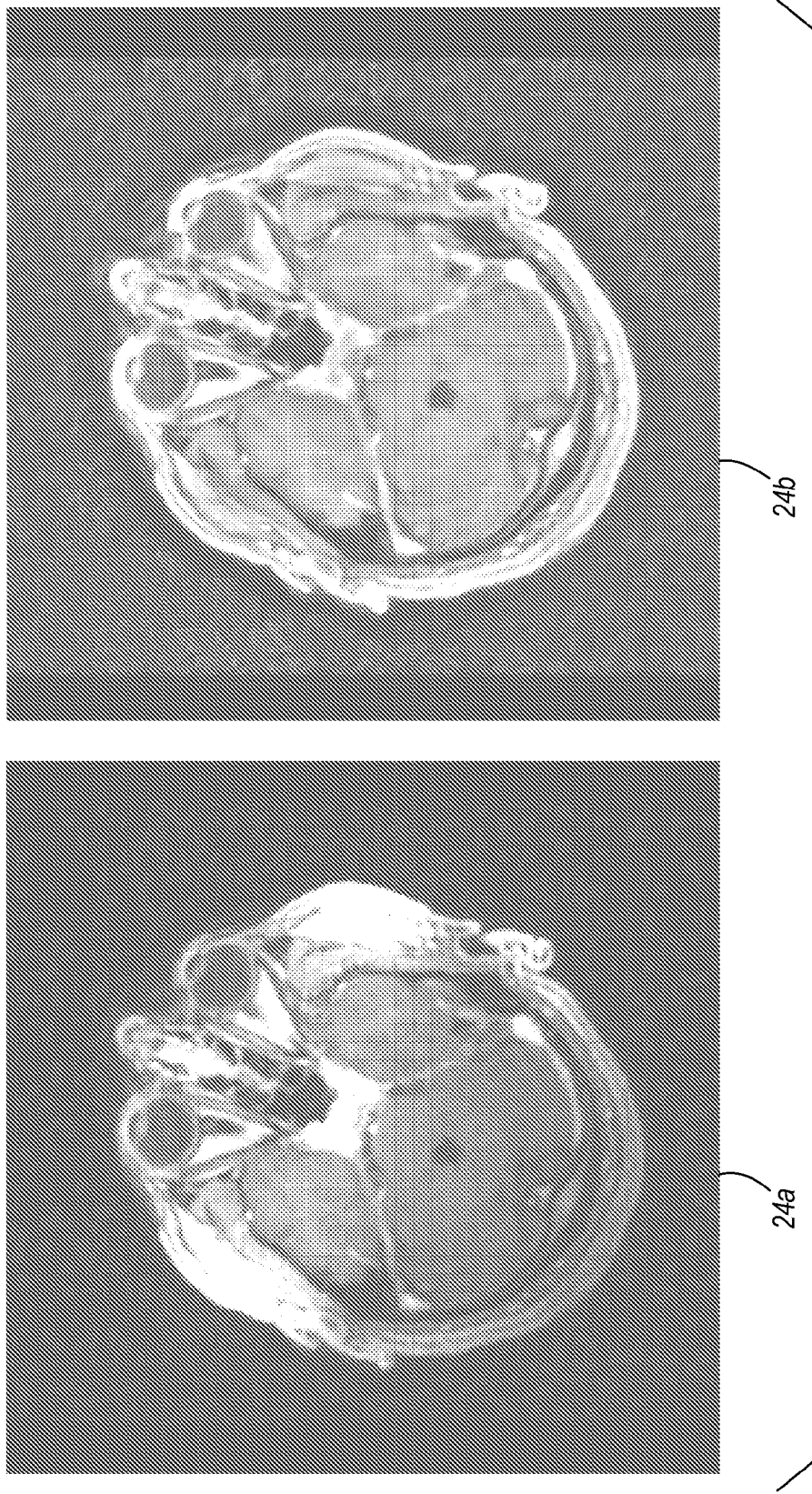
FIG. 2 is an axial image slice from FIG. 1 before and after brightness equalization.

Brightness equalization is optionally applied to the selected axial image slices. This is generally only necessary if the images are not uniformly bright to begin with. For example, MR images often suffer from significant non-uniform brightness, whereas CT images do not. FIG. 2 illustrates an axial image slice before 24a and after 24b brightness equalization. The purpose of brightness equalization is to produce a better, more complete edge mask (explained below). Brightness equalization is a common operation in the field of image processing, and can be performed in a variety of ways. A standard reference is "Image Processing, Analysis, and Machine Vision" by Sonka, Hlavac, and Boyle.

One such method of brightness equalization is executed as follows: given an input image X, first create an auxiliary image Y by convolving image X with a Gaussian kernel whose size is L/f, where L is larger of the width of X and the height of X. The factor f=20 has been found to give good results for the purposes of this AC-PC segmentation method, but any similar value that is roughly in the range 10 to 30 could be used as well. The brightness-equalized image Z is then calculated as $Z=X*(Ymin+D)/(Y+D)$ where $D=(Ymax-K*Ymin)/(K-1),$ and K is a parameter that controls the amount of equalization. Ymin is the minimum pixel value in image Y, and Ymax is the maximum pixel value in image Y. The parameter K=3 has been found to provide adequate equalization without unacceptably increasing the image noise, which is a common, however undesirable side-effect of brightness equalization.

Figure 3:
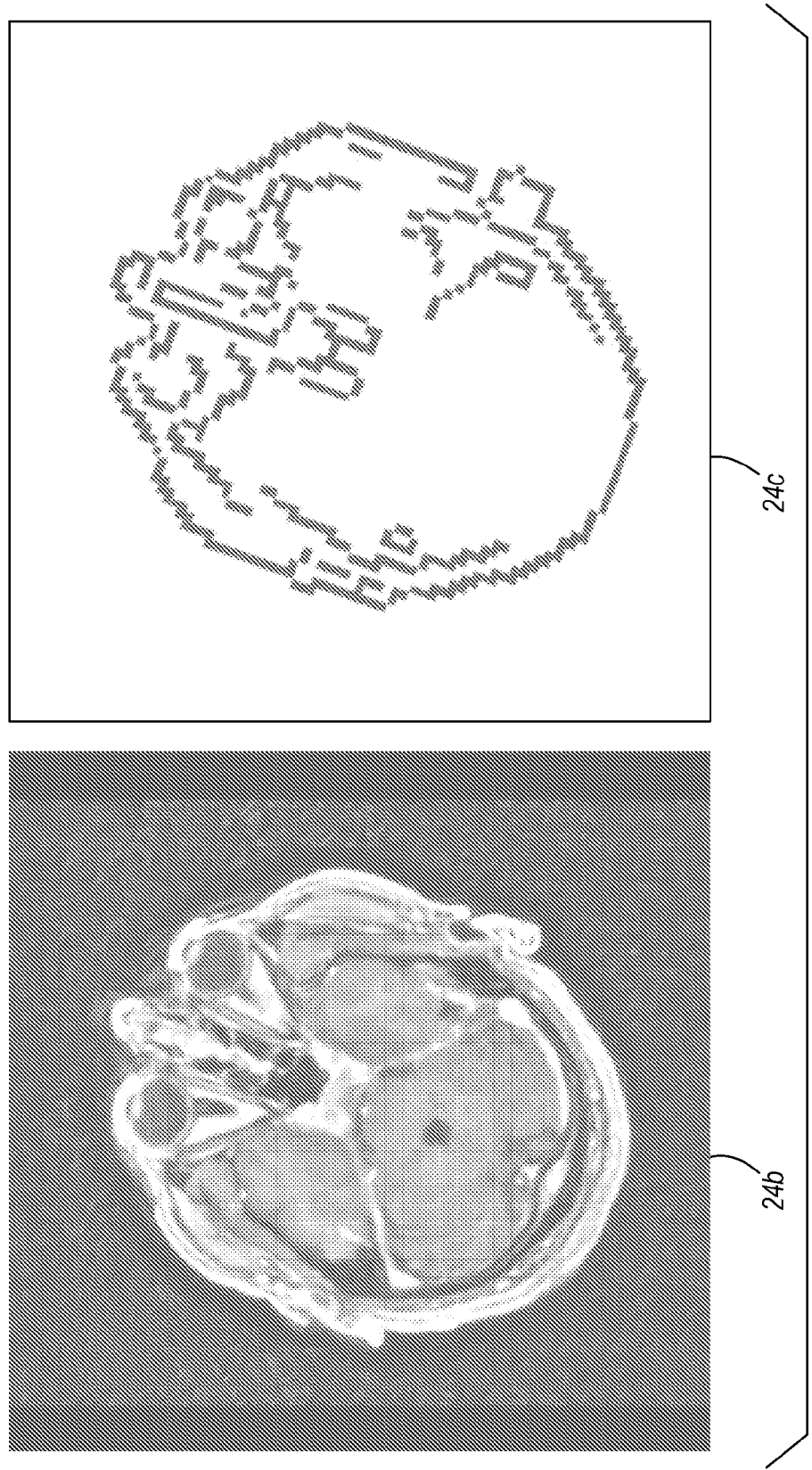
FIG. 3 is an edge mask created from the brightness equalized axial image slice from FIG. 2.

Continuing with phase one, an edge mask of each selected axial image slice is created. FIG. 3 illustrates the brightness-equalized image 24b and its edge mask 24c. As with brightness equalization, there are several well-known techniques for creating an edge mask from an image. The results of AC-PC segmentation by the method disclosed herein do not depend strongly on the particular technique that is chosen. The Canny algorithm is a well-known and effective method used to produce an edge mask (J. Canny, "A computational approach to edge detection," IEEE Trans. Pattern Anal. Machine Intell., 8, pp. 679-698, 1986).

Figure 4:
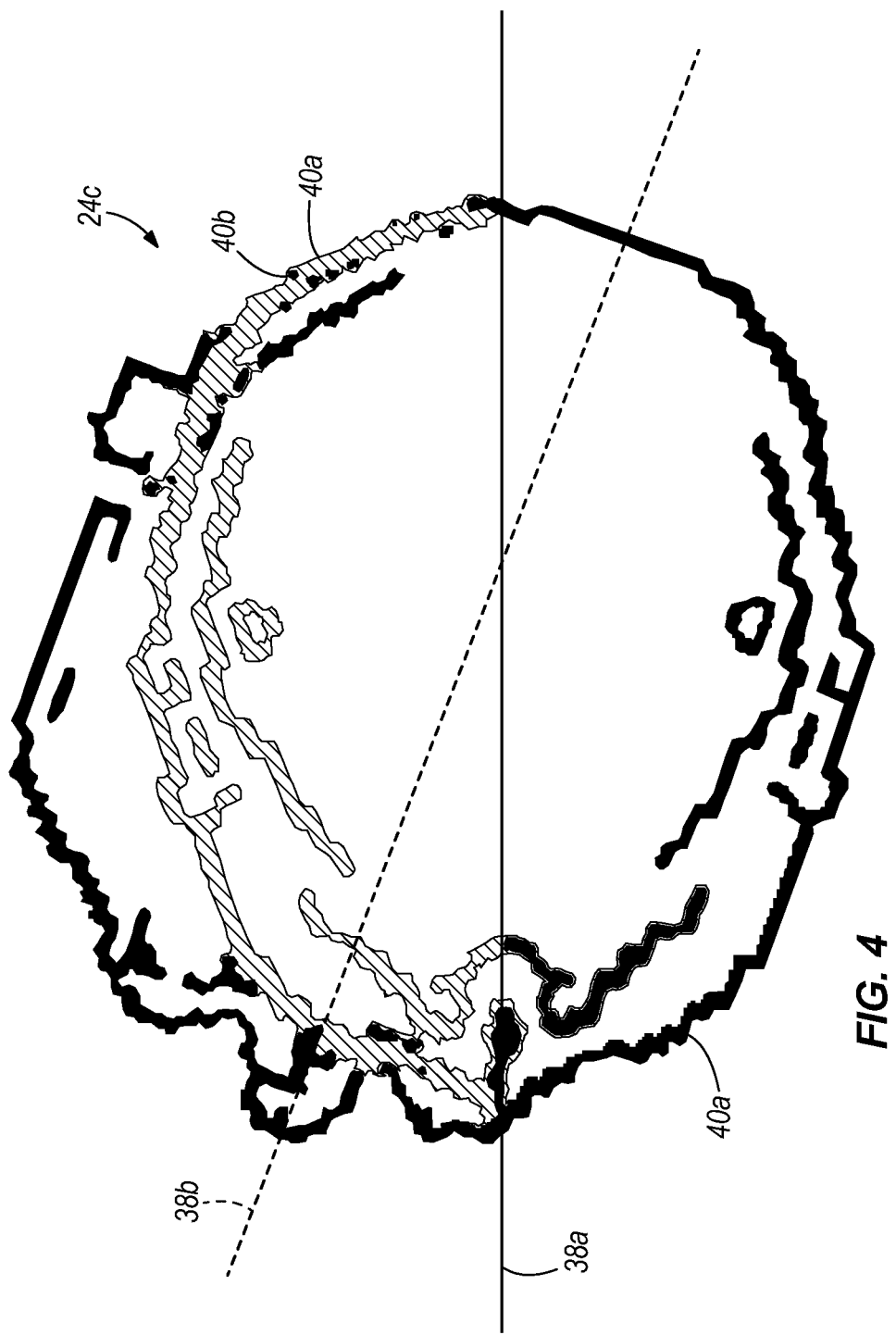
FIG. 4 is an edge mask of an axial image slice reflected over a tentative symmetry axis.

The symmetry axis of each axial image slice 24b (and its corresponding edge mask 24c) is determined as follows (FIG. 4). A tentative symmetry axis 38a is selected, each pixel 40a on one half of the edge mask is reflected through the tentative symmetry axis 38a, and one point is scored for each reflected pixel 40a that lands on another pixel 40b of the edge mask. These steps are iterated over a range of tentative symmetry axes, and the actual symmetry axis 38b is identified as the one that produces the highest score. This method of identifying the symmetry axis of each edge mask is less computationally complex and consequently many times faster than other known methods without sacrificing accuracy.

Figure 5:
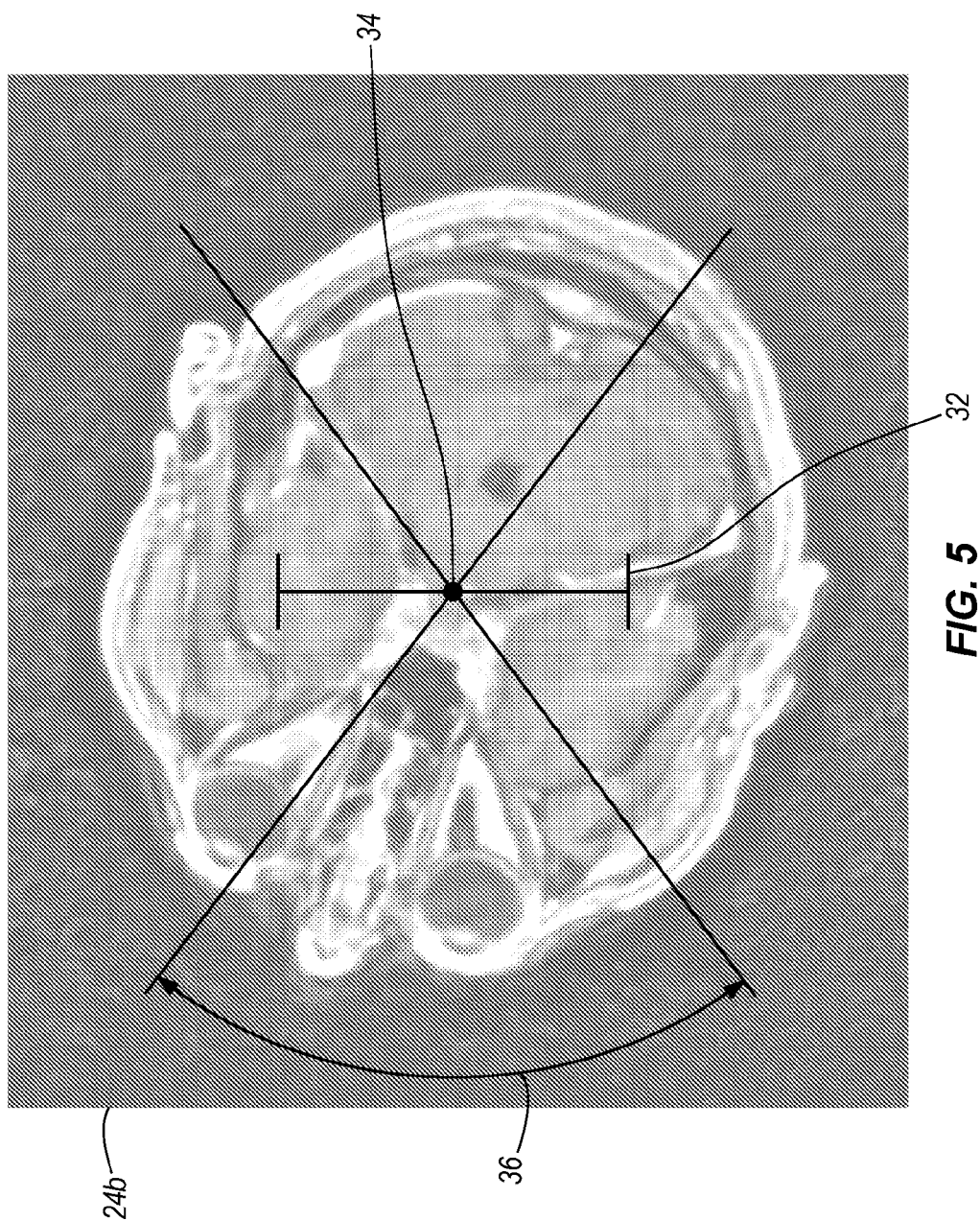
FIG. 5 illustrates the ranges of tentative symmetry axis parameters on the brightness equalized axial image slice from FIG. 2.

As illustrated in FIG. 5, the iteration range for the purposes of this AC-PC segmentation method includes a range of values 32 for the center point 34 of the tentative axes. The center point 34 is moved away from the image center by +/−20% of the image width, with a step size of 1 pixel. Also, for each center point 34 within the specified range 32, axis angles within a range 36 of +/−30° of the vertical with a step size of 1° are included in the iterative process. The step size does not need to be extremely small because the MSP orientation is refined later in phase three of the method. These parameters are dictated by the required precision of the particular application and reasonable expectations about the imaging scenario. In particular, the head is expected to be nearly vertical in these images because the patient is lying face up in the scanner. However, this method for finding the symmetry axis would work for any angle-range and step size, though computation time becomes longer as the range increases and the step size decreases.

Figure 6:
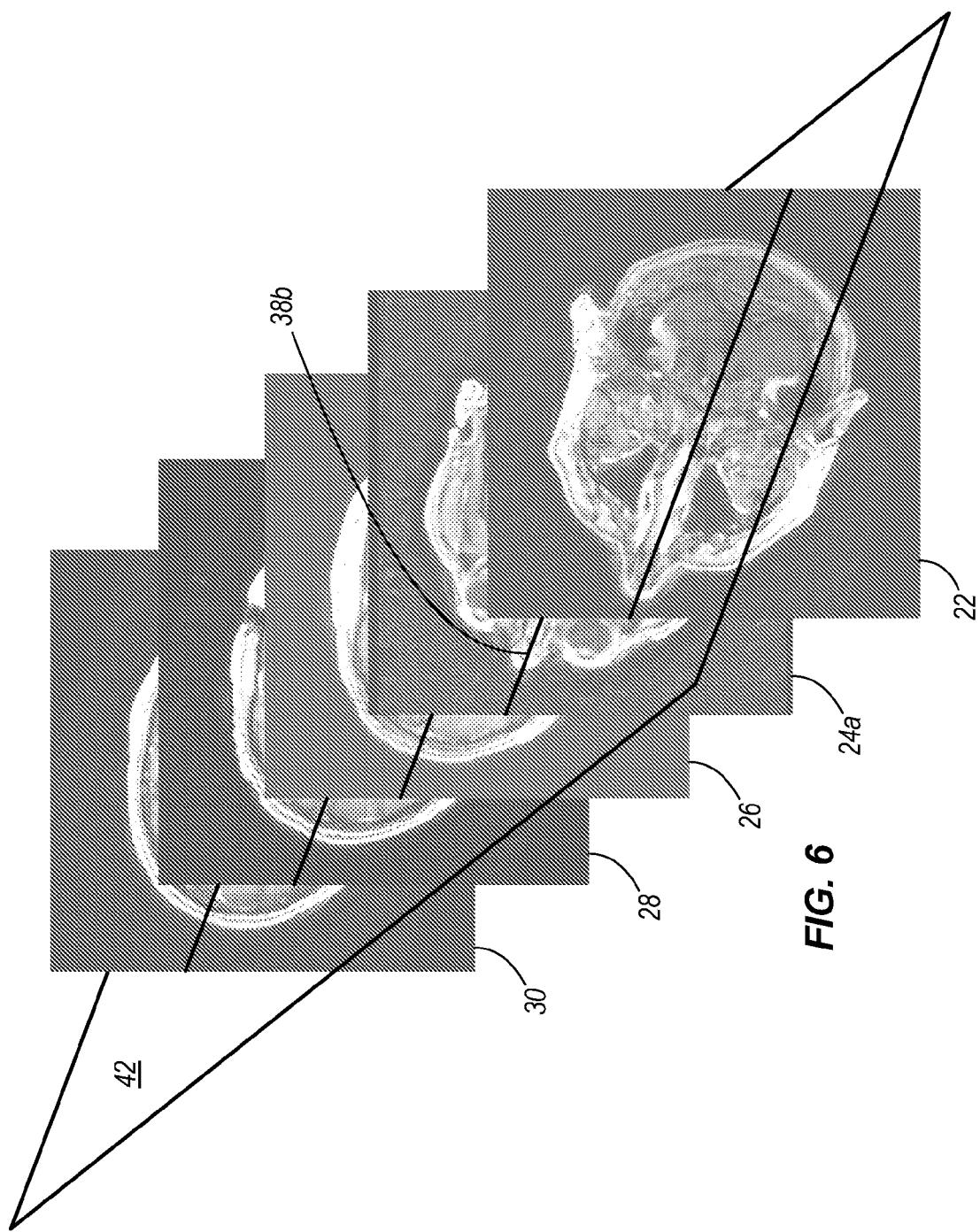
FIG. 6 illustrates the series of axial image slices from FIG. 1 with symmetry axes fit to a plane.

FIG. 6 illustrates the symmetry axes of the axial image slices 22, 24b, 26, 28, 30 fitted to a single plane 42 using a robust regression method. This plane 42 is taken to be the estimate (or approximation) of the MSP. Robust regression is a well-known technique for fitting a set of data points (in this case, the axis angles and center points) to a parameterized function (in this case, a plane). Robust regression is more computationally demanding than ordinary regression, but is often more accurate.

Figure 7:
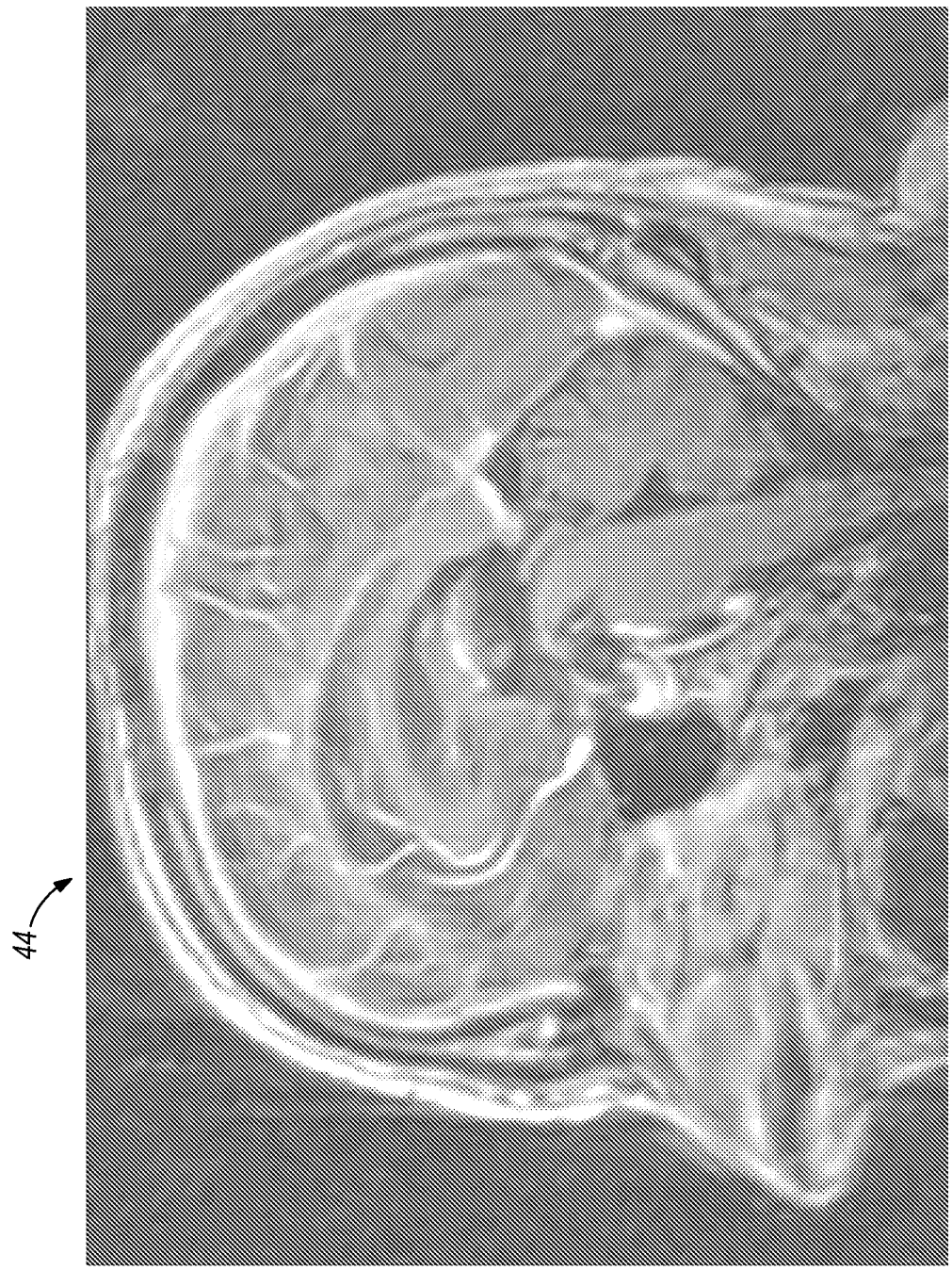
FIG. 7 is an image slice taken along the mid-sagittal plane estimate.
Figure 8:
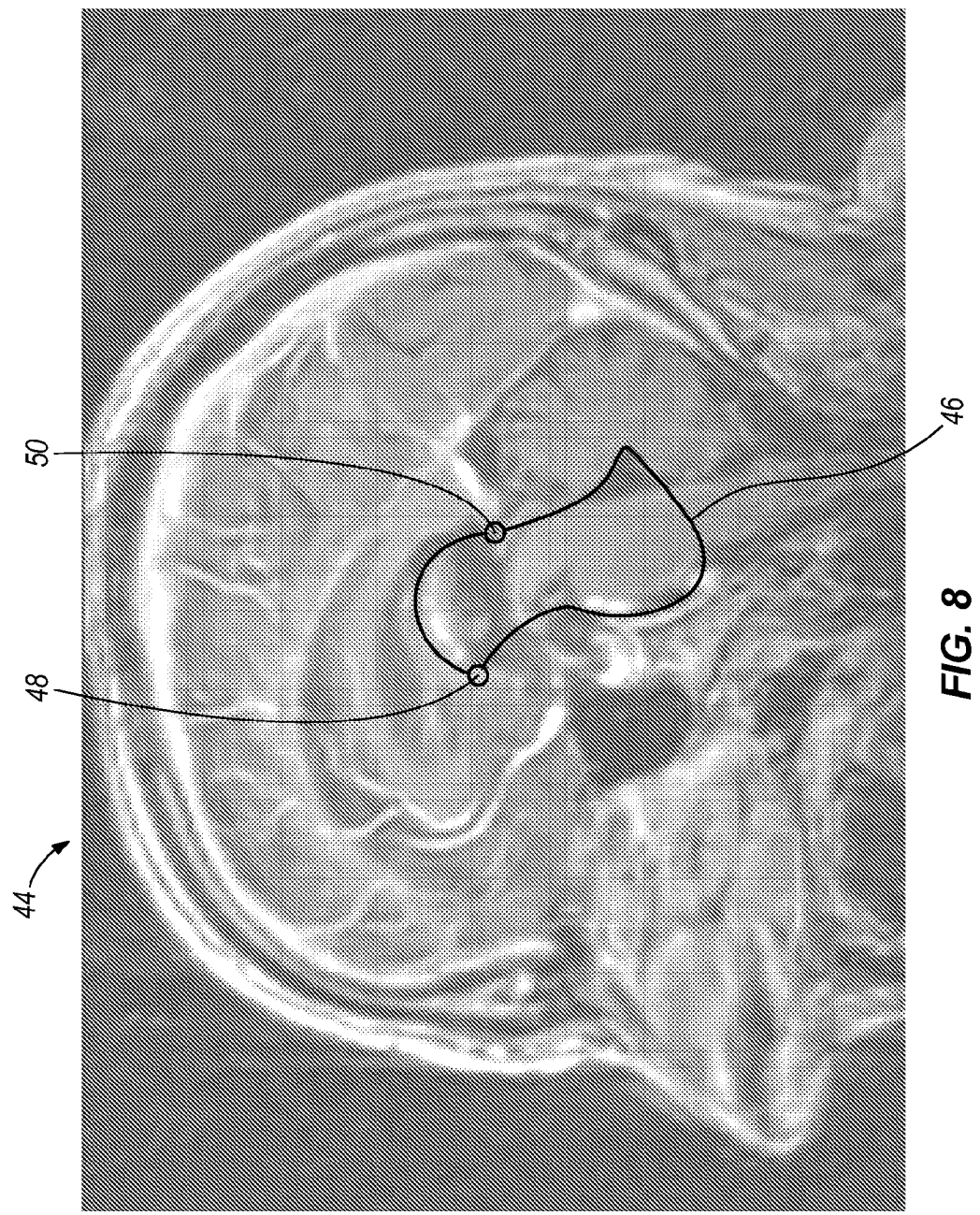
FIG. 8 illustrates the active appearance model of the brainstem region applied to the image from FIG. 7.

The second phase, approximation of the AC and PC points, begins by reformatting the volumetric image data onto the MSP estimate in order to extract a MSP image 44 as shown in FIG. 7. An active appearance model (AAM) of the brainstem and third ventricle region 46 is applied to the MSP image 44 as shown in FIG. 8. The process of obtaining an AAM is yet another widely known method (T. F. Cootes, G. J. Edwards, and C. J. Taylor, "Active appearance models," IEEE Trans. Pattern Anal. Machine Intell I, 23(6):681-685, 2001). Once the AAM 46 has found the best match for its internal model on the MSP image 44, the AC and PC point estimates 48, 50 are identified at locations in the image corresponding to locations identified in the model.

The use of an AAM to identify anatomical structures in images has several advantages over "binary" methods. For example, the AAM uses all of the grayscale information in the image, whereas binary methods convert the image to black and white, which entails a loss of information and also requires a choice for the threshold. Usually it is difficult if not impossible to find a threshold that works well across many images for this purpose. Further, the accuracy of AAM results can often be improved by training the model on additional images. There is no corresponding way to improve the results of the binary methods. The choice of the brainstem and third ventricle region for the AAM was arrived at by inspecting a large number of brain images for anatomical features that are both relatively constant across subjects and are recognizable by the AAM method, and was verified and fine-tuned by analyzing the segmentation results on a set of test images. In the case that an anatomical anomaly was expected in this region (e.g., as a result of pathology), an AAM of a different brain structure can be used to identify the AC and PC point estimates. Alternatively, application of an AAM of a different brain structure can be used to verify that the AC and PC point estimates given by application of the brainstem and third ventricle AAM are acceptable approximations.

Figure 9:
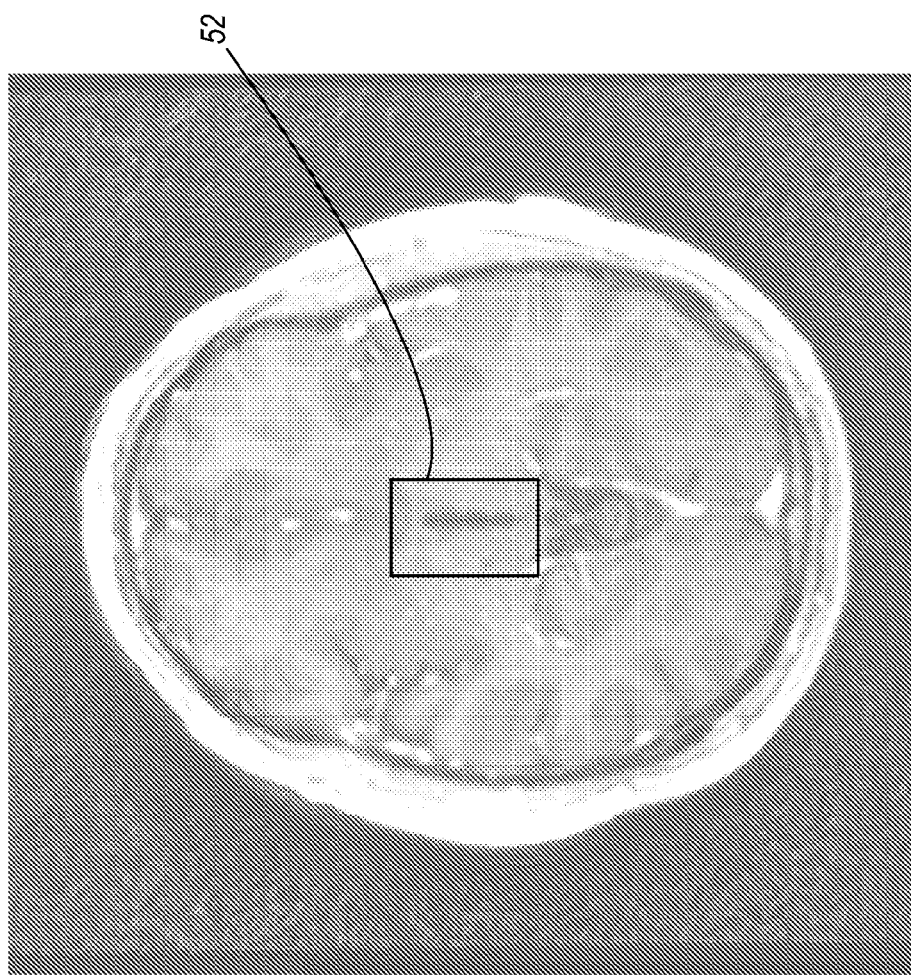
FIG. 9 is an axial image slice taken along a plane including the AC and PC point estimates.

The third phase, refining the MSP, begins by reformatting the volumetric image data onto an axial plane passing through the AC and PC point approximations (FIG. 9). The resulting image is cropped to a region 52 just large enough to surround the AC and PC point estimates 48, 50 and a portion of the third ventricle 54. The width of the cropped image is taken to be 0.8 times the AC-PC separation distance, and the height of the cropped image is taken to be 1.1 times the AC-PC separation distance. However, in other embodiments, the dimensions of the cropped image can vary from these parameters.

Figure 10:
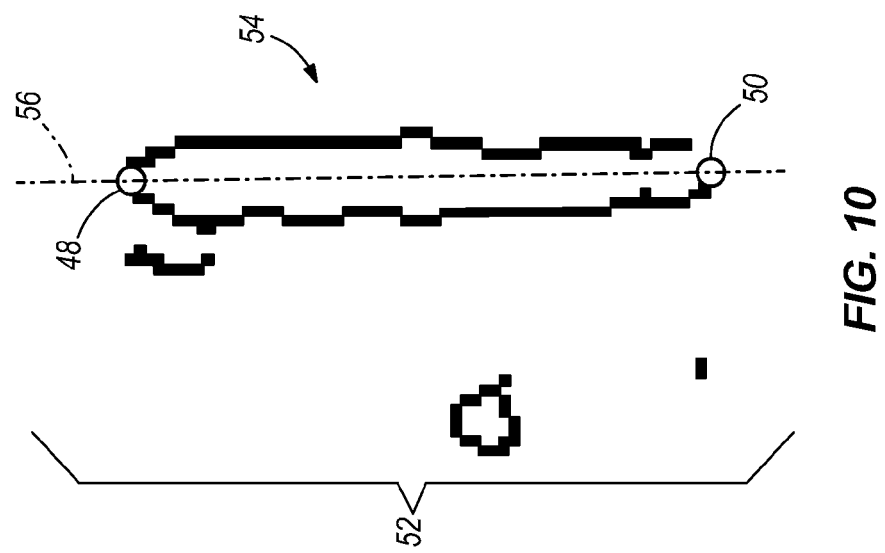
FIG. 10 is an edge mask of a portion of the image from FIG. 9.

An edge mask (FIG. 10) is created from the cropped image using the Canny algorithm or another comparable method known in the art. The symmetry axis 56 of the edge mask is identified using the technique discussed above in the first phase. The orientation of the symmetry axis 56 gives the refined MSP.

Figure 11:
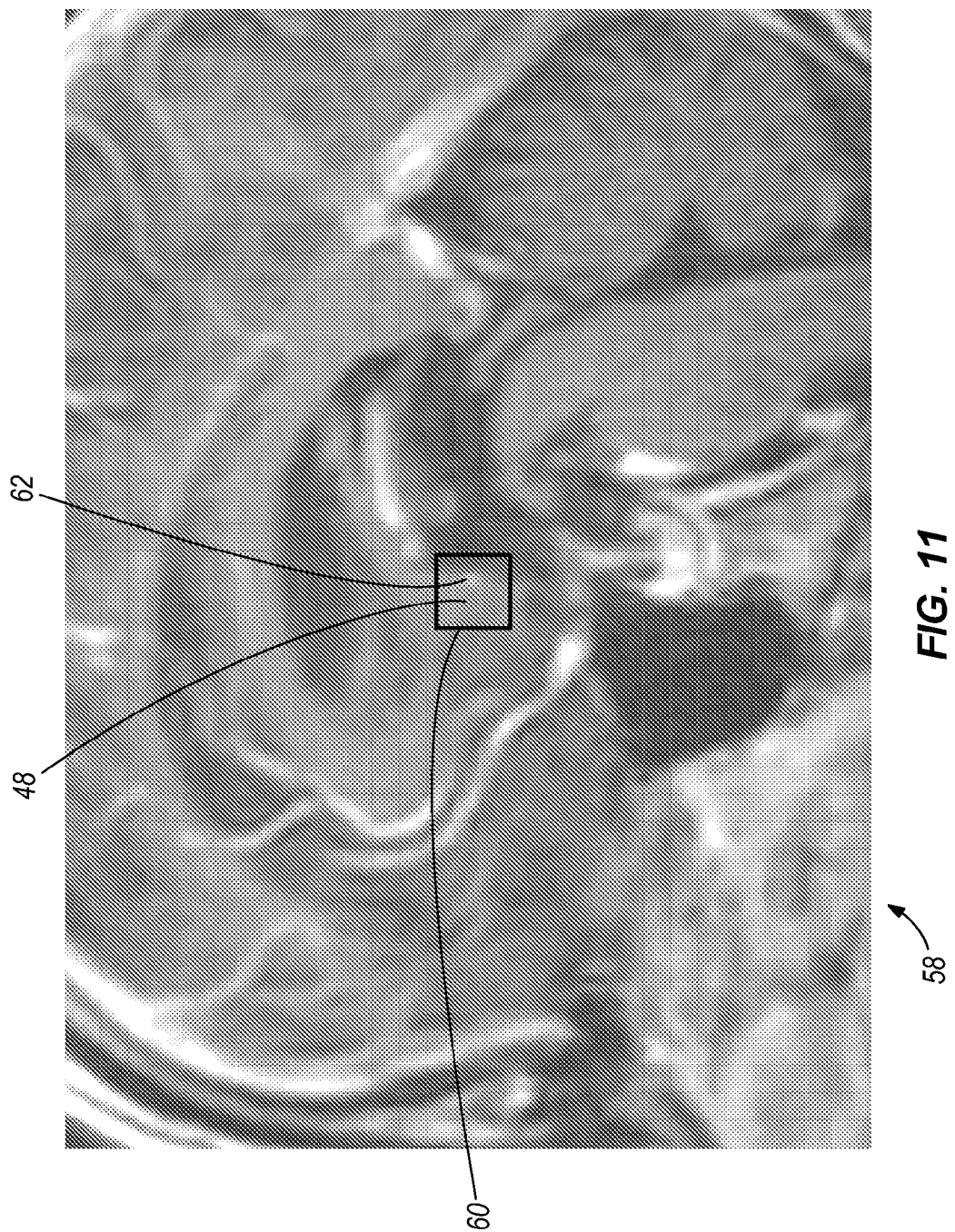
FIG. 11 illustrates the AC estimate and AC point in a refined mid-sagittal plane image slice.
Figure 12:
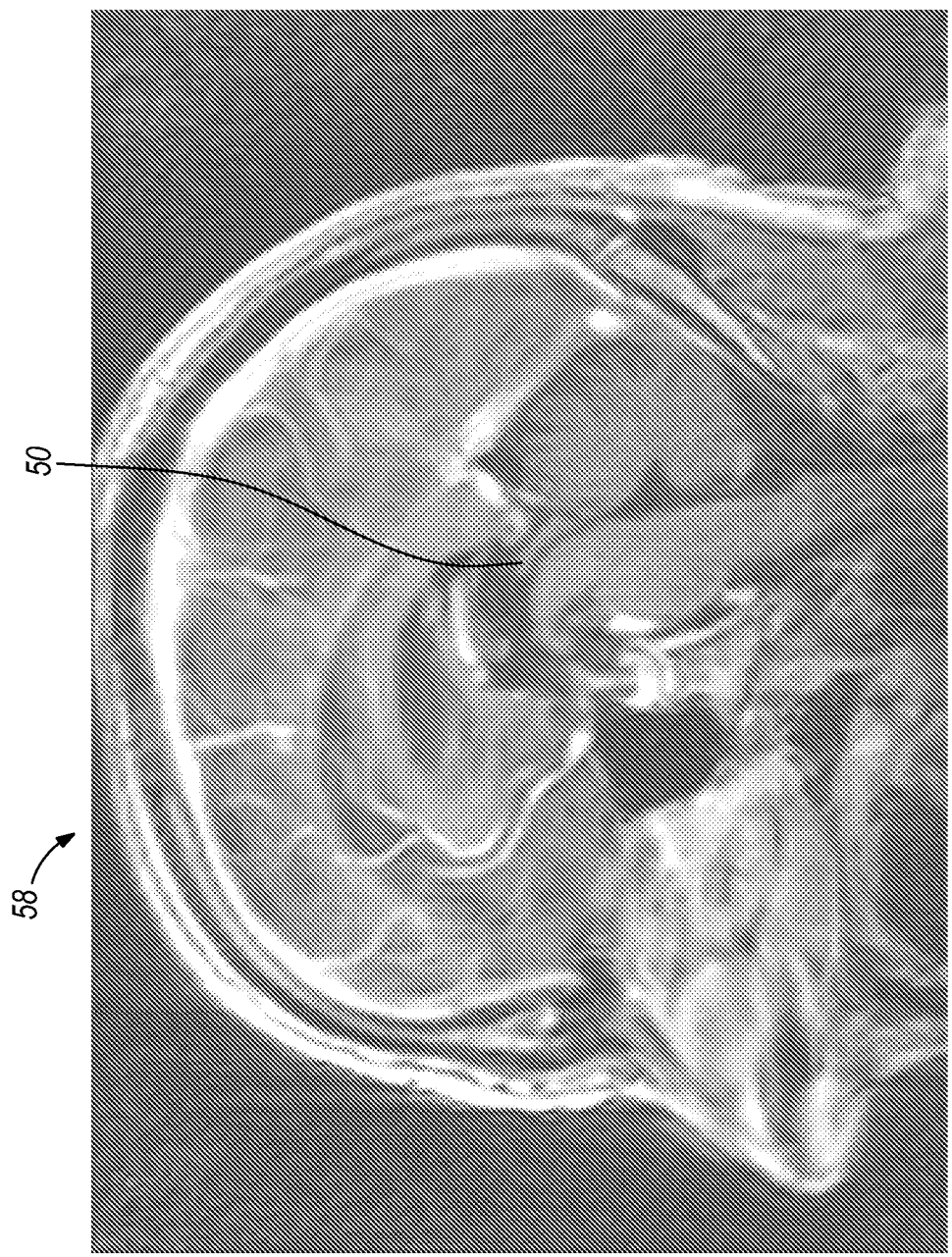
FIG. 12 illustrates the PC estimate in a refined mid-sagittal plane image slice.

The fourth phase, refining the AC point, begins by reformatting the volumetric image data onto the refined MSP in order to extract a refined MSP image 58, which is shown in FIGS. 11 and 12. The AC estimate 48 from phase two is projected onto the refined MSP image 58, and a rectangular region 60 approximately 6 mm×6 mm and centered at the projected AC estimate 48 is identified. The brightest peak within this region is taken to be the AC point 62.

Figure 13:
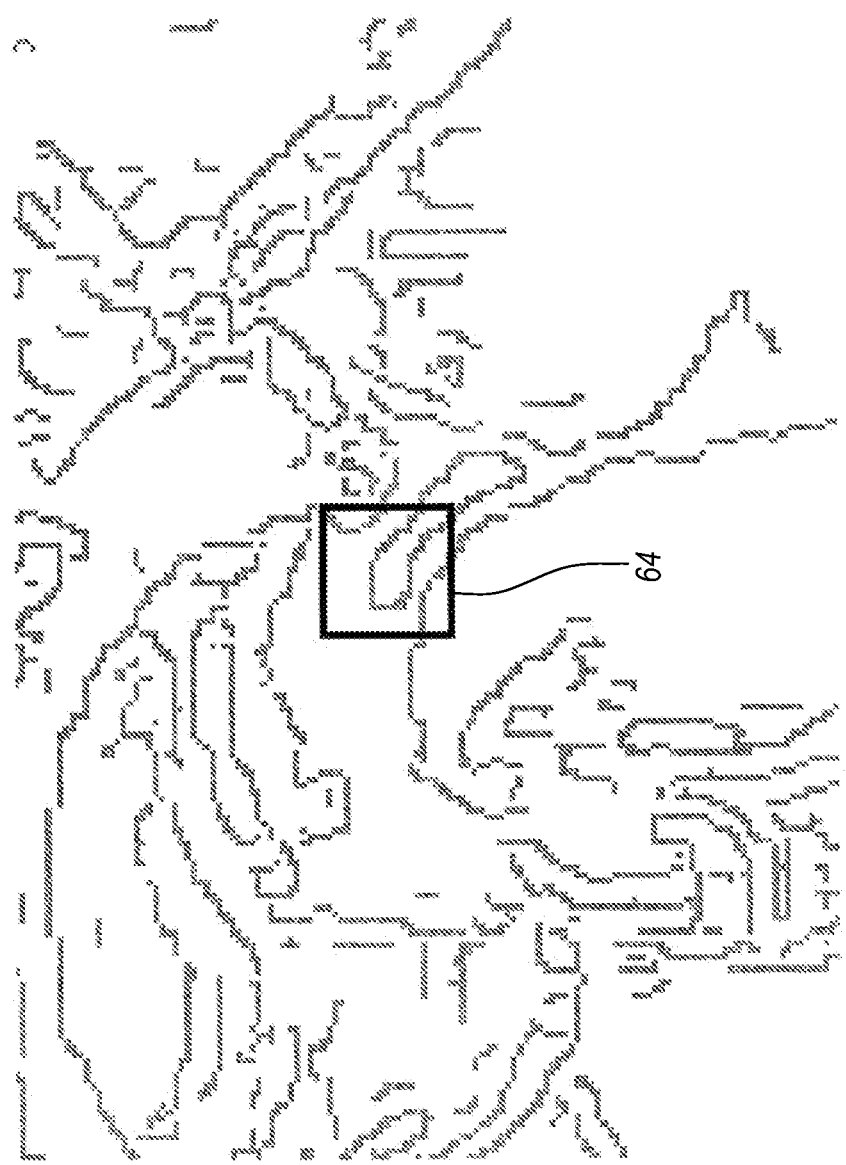
FIG. 13 is an edge mask of the refined mid-sagittal plane image slice.
Figure 14:
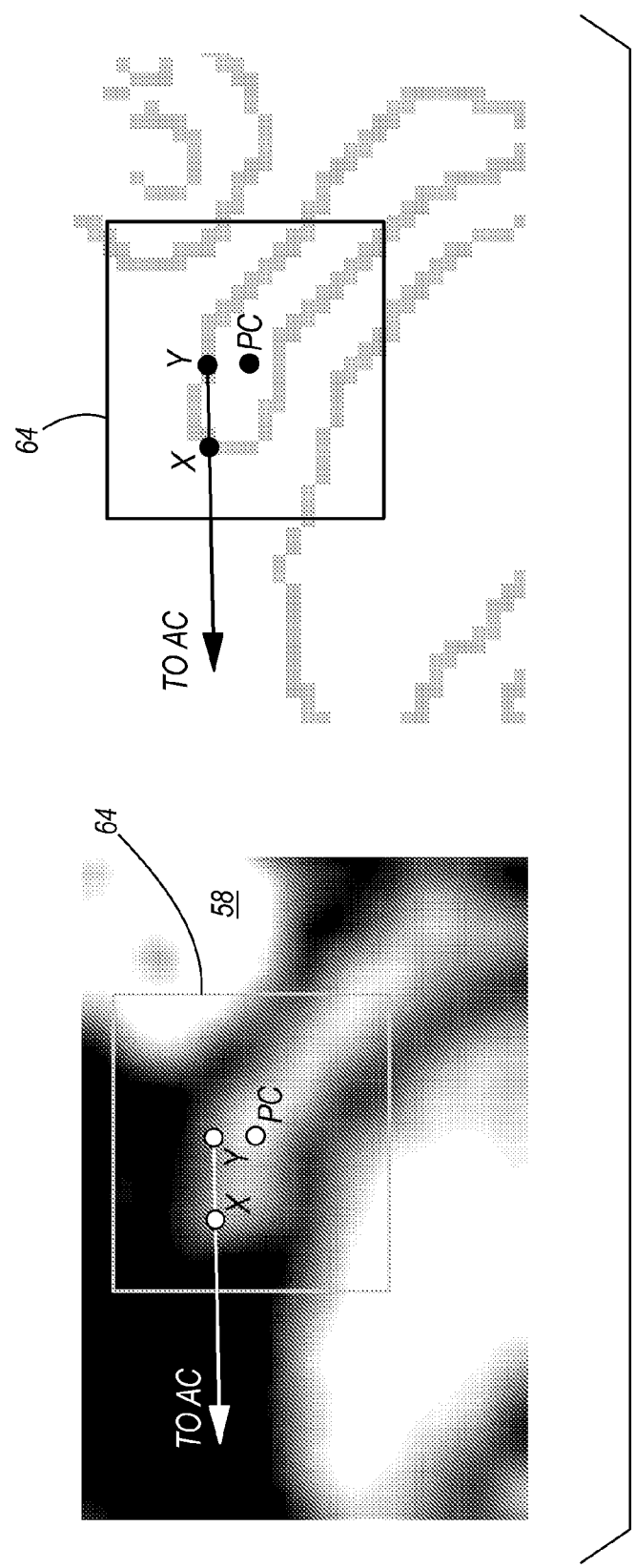
FIG. 14 includes close-ups of the refined mid-sagittal plane image from FIG. 12 and the edge mask from FIG. 13.

The fifth phase, refining the PC point, begins by projecting the PC estimate 50 from phase two onto the refined MSP image 58, as shown in FIG. 12. An edge mask (FIG. 13) is created from the image using the Canny algorithm or another comparable method known in the art, and a rectangular region 64 approximately 6 mm×6 mm centered around the projected PC estimate 50 is identified. In FIG. 14, three points are identified (X, Y, PC) which correspond to the three stages involved in identifying the PC point from the edge mask (FIG. 13). Point X is the point on the edge mask for which the line AC-X is most nearly parallel to the image gradient at X. Point Y is obtained by translating point X 1 mm along the AC-X line, away from AC. Finally, the PC point is identified as the largest intensity peak along the line that passes through Y and that is perpendicular to the AC-Y line.

Figure 15:
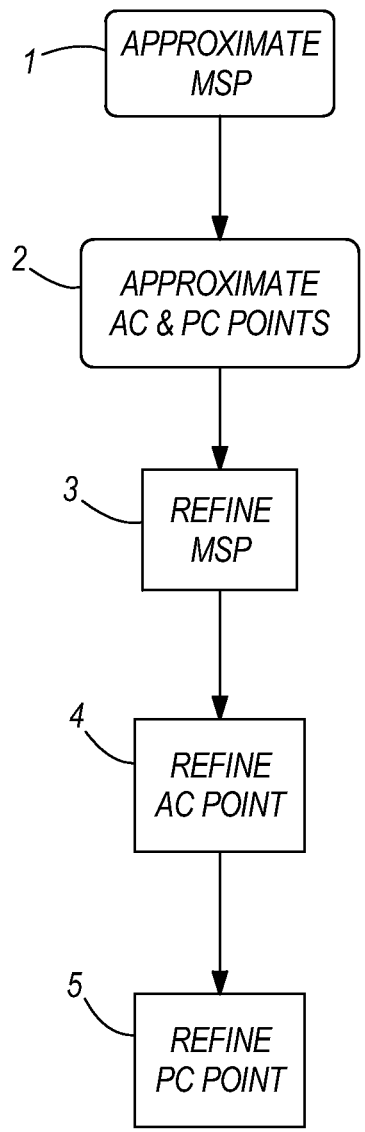
FIG. 15 is a flow chart that illustrates the phases and steps of the AC-PC system and method according to one embodiment of the present invention.

FIG. 15 is a flow chart illustrating the phases and steps of the AC-PC segmentation method discussed above.

Figure 16:
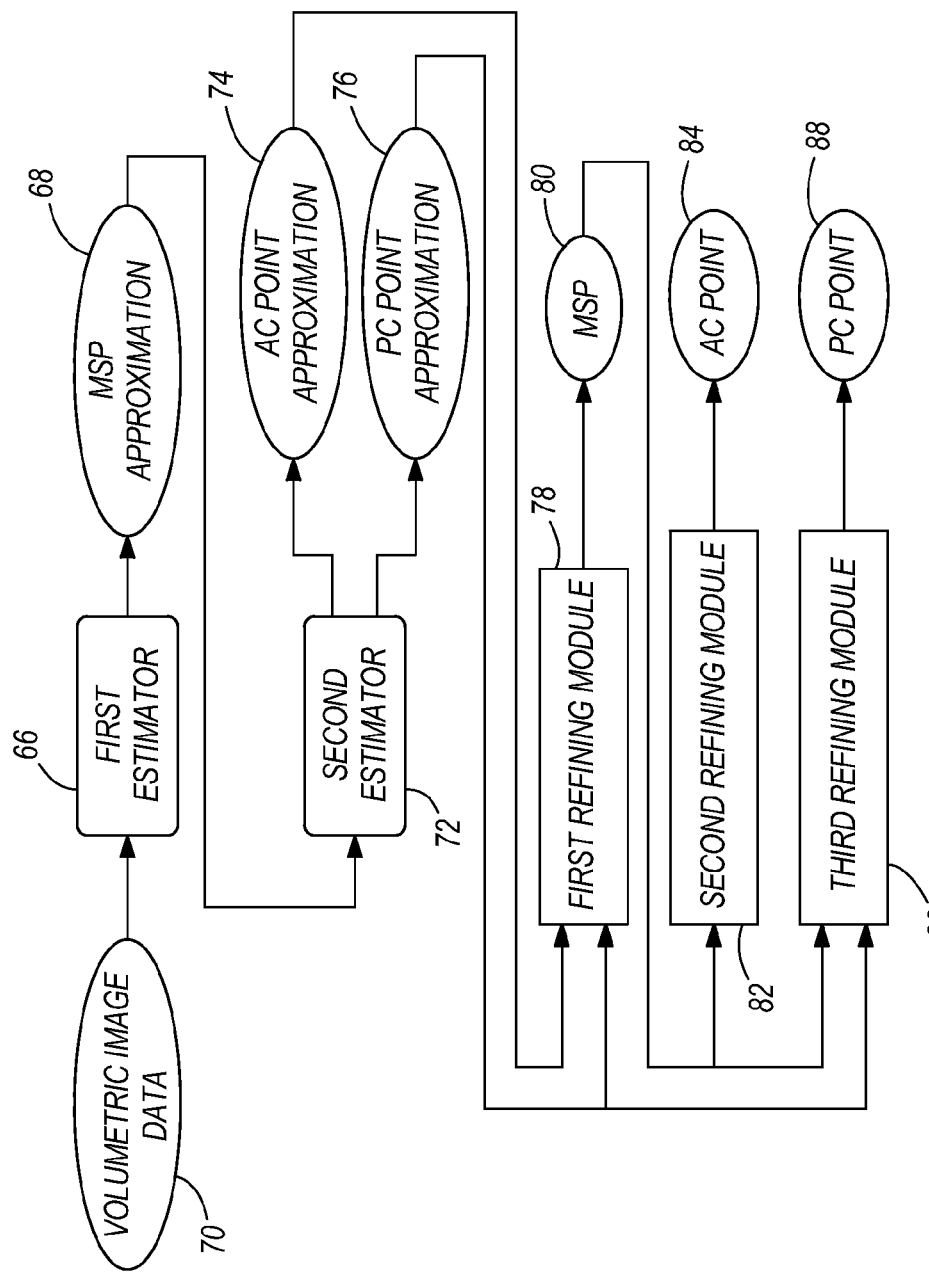
FIG. 16 illustrates the AC-PC system according to one embodiment of the present invention.

As shown in FIG. 16, the AC-PC segmentation system can be implemented in a modular format. Each module is represented by a rectangular or rounded-corner rectangular box. The input and output data is represented by ovals—input data enters each module on the left-hand side, and output data exits each module on the right-hand side of the figure. Arrows indicate the movement of data through the system. The system functions as follows. A first estimator 66 determines a mid-sagittal plane approximation 68 from the volumetric neuroradiological image data 70. A second estimator 72 determines AC and PC point approximations 74, 76 from the mid-sagittal plane approximation 68. A first refining module 78 identifies the mid-sagittal plane 80 using the AC and PC point approximations 74, 76 as input data. A second refining module 82 identifies the AC point 84 from the mid-sagittal plane 80, and a third refining module 86 identifies the PC point 88 from the mid-sagittal plane 80 and the AC point 84.

In some embodiments, identification of the mid-sagittal plane, AC and PC via implementation of the method discussed above can serve many purposes including, but not limited to, use as input data to merge images of a subject from a plurality of imaging modalities; in interventional radiological equipment for treatment planning, subject positioning, and the like; for neuroradiological research, etc. The system and method can also be used to find AC and PC points in neuroradiological volumetric images of some animals, though certain parameters of the method require adjustment. For example, the tentative symmetry axis ranges differ based upon the positioning/orientation of the animal subject's head in the scanner.

In some embodiments, this system and method can be implemented within a picture archiving and communications system (PACS) to, for example, facilitate image normalization across subjects, or any of a wide range of objectives such as those discussed above. Alternatively or in addition, the system and method can be part of a software-implemented segmentation tool kit. This tool kit or application software implementing the method can be installed on a stand-alone computer work station or a server accessible by work stations over a network. In another embodiment, a computer-readable medium encoded with instructions to carry out the AC-PC segmentation method disclosed can be used in a mobile device such as a PDA or laptop computer. In other embodiments, the system and method can be implemented as an automated function of an imaging modality. As such, the volumetric neuroradiological image data can be reformatted to a standard format for viewing or storage. A standard format can include several image slices at various locations and planes of interest.

Various features and advantages of the invention are set forth in the following claims.

What is claimed is:

1. A method for processing an image, the method comprising
   creating, by a computer, a two-dimensional edge mask of each of a plurality of axial image slices included in a volumetric image;
   identifying, by the computer, a symmetry axis of each two-dimensional edge mask; and
   fitting, by the computer, a plane to the symmetry axes, the plane defining a mid-sagittal plane estimate,
   wherein identifying the symmetry axis of each two-dimensional edge mask includes, for each two-dimensional edge mask,
      identifying a plurality of tentative symmetry axes for the two-dimensional edge mask,
      generating a total score for each of the plurality of tentative axes based on the two-dimensional edge mask, and
      identifying the tentative axis with the highest total score as the symmetry axis for the two-dimensional edge mask.

2. The method of claim 1, further comprising extracting a mid-sagittal image from the volumetric image based on the mid-sagittal plane estimate and determining an anterior commissure (AC) point and a posterior commissure (PC) in the mid-sagittal plane image.

3. The method of claim 2, wherein determining the AC point and the PC point in the mid-sagittal plane image includes:
 determining the AC point and the PC point in the mid-sagittal plane image;
 determining a refined mid-sagittal plane estimate based on the AC point and the PC point;
 extracting a refined mid-sagittal plane image from the volumetric image based on the refined mid-sagittal plane estimate; and
 updating at least one of the AC point and the PC point based on the refined mid-sagittal plane image.

4. The method of claim 3, wherein updating at least one of the AC point and the PC point includes updating the PC point based on the refined mid-sagittal plane image and the AC point.

5. The method of claim 3, wherein determining the AC point and the PC point comprises applying an active appearance model to the mid-sagittal plane image.

6. The method of claim 5, wherein applying an active appearance model to the mid-sagittal plane image includes applying one selected from the group comprising a brainstem and third ventricle region to the mid-sagittal plane image.

7. The method of claim 3, wherein determining the refined mid-sagittal plane estimate comprises:
 reformatting a plurality of axial image slices onto a plane which is perpendicular to the mid-sagittal plane estimate and which passes through the AC point and the PC point;
 extracting an axial plane image;
 cropping the axial plane image to a region including the AC point and the PC point and at least a portion of a brain ventricle extending therebetween;
 creating an edge mask of the cropped axial plane image; and
 identifying a symmetry axis of the cropped axial plane image.

8. The method of claim 7, wherein identifying the symmetry axis of the cropped axial plane image comprises:
 (a) identifying a tentative symmetry axis, the tentative symmetry axis defining first and second halves of the edge mask;
 (b) reflecting each pixel of the first half of the edge mask over the tentative symmetry axis;
 (c) scoring one point for each pixel which lands on the second half of the edge mask; and
 (d) adding each point into a total score for the tentative symmetry axis;
 the method further comprising, iterating acts (a), (b), (c), and (d) for each of a range of tentative symmetry axes; and identifying the tentative symmetry axis with the highest total score as the symmetry axis.

9. The method of claim 3, wherein updating at least one of the AC point and the PC point comprises:
 projecting the AC point onto the refined mid-sagittal plane image;
 identifying a brightness peak within a region surrounding the projected AC point; and
 updating the AC point based on the brightness peak.

10. The method of claim 3, wherein updating at least one of the AC point and the PC point comprises:
 projecting the PC point onto the refined mid-sagittal plane image;
 creating an edge mask of the refined mid-sagittal plane image;
 identifying a point X within a region surrounding the projected PC point, which lies on the edge mask, and for which a gradient of the refined mid-sagittal plane image is approximately parallel to a direction from the AC point to the point X;
 obtaining a point Y by translating the point X along the direction from the AC point to the point X;
 identifying an intensity peak in a direction perpendicular to the direction from the AC point to Y; and
 updating the PC point based on the intensity peak.

11. The method of claim 1, further comprising equalizing brightness of the plurality of axial image slices prior to creating the edge mask.

12. The method of claim 1, wherein creating the edge mask of each of the plurality of axial image slices included in the volumetric image includes creating an edge mask of each of a plurality of slices in a vertical range from a medulla to a top of a corpus calossum.

13. The method of claim 1, wherein generating the total score for each of the plurality of tentative symmetry axes based on the two dimensional edge mask includes, for each of the plurality of tentative symmetry axes:
 (a) defining a first half of the edge mask and a second half of the two-dimensional edge mask based on the tentative symmetry axis;
 (b) reflecting each pixel of the first half of the two-dimensional edge mask over the tentative symmetry axis;
 (c) scoring one point for each pixel which lands on the second half of the two-dimensional edge mask; and
 (d) adding each point into a total score for the tentative symmetry axis.

14. An image processing system comprising:
 a computer; and
 a module executable by the computer and configured to:
  create a two-dimensional edge mask of each of a plurality of axial image slices included in the volumetric image,
  identify a symmetry axis of each two-dimensional edge mask,
  fit a plane to the symmetry axes,
  determine a mid-sagittal plane estimate based on fitting a plane to the symmetry axis, and
  extract a mid-sagittal plane approximation based on the mid-sagittal plane estimate,
 wherein the module identifies the symmetry axis of each two-dimensional edge mask by, for each two-dimensional edge mask
  identifying a plurality of tentative symmetry axes for the two-dimensional edge mask,
  generating a total score for each of the plurality of tentative axes based on the two-dimensional edge mask, and
  identifying the tentative axis with the highest total score as the symmetry axis for the two-dimensional edge mask.

15. The image processing system of claim 14, further comprising:
 a second module executable by the computer and configured to identify a mid-sagittal plane image included in the volumetric image using an anterior commissure (AC) point approximation and a posterior commissure (PC) approximation;
 a third module configured to identify a AC point based on the mid-sagittal plane image; and
 a fourth module configured to identify a PC point based on the mid-sagittal plane image and the AC point.

16. The image processing system of claim 14, further comprising:
a second module configured to determine an anterior commissure (AC) point approximation and a posterior commissure (PC) point approximation based on the mid-sagittal plane approximation.

17. The image processing system of claim 14, wherein the first module is further configured to equalize brightness of the plurality of axial image slices prior to creating the edge mask.

18. A non-transitory computer readable medium encoded with a plurality of processor-executable instructions for performing image processing, the instructions including instructions for:
creating a two-dimensional edge mask of each of a plurality of axial image slices included in a volumetric image;
identifying a symmetry axis of each two-dimensional edge mask;
fitting a plane to the symmetry axes, the plane defining a mid-sagittal plane estimate; and
extracting a mid-sagittal plan image from the volumetric image based on the mid-sagittal plane estimate;
wherein identifying a symmetry axis of each two-dimensional edge mask includes, for each two-dimensional edge mask
identifying a plurality of tentative symmetry axes for the edge mask,
generating a total score for each of the plurality of tentative axes based on the two-dimensional edge mask, and
identifying the tentative axis with the highest total score as the symmetry axis for the two-dimensional edge mask.

19. The computer readable medium of claim 18, further comprising instructions for:
estimating an anterior commissure (AC) point and a posterior commissure (PC) point in the mid-sagittal plane image;
determining a refined mid-sagittal plane based on the AC point and the PC point to extract a refined mid-sagittal plane image; and
updating at least one of the AC point and the PC point based on the refined mid-sagittal plane image.

20. The computer readable medium of claim 19, wherein the instructions for updating at least one of the AC point and the PC point include instructions for updating the PC point based on the refined mid-sagittal plane image and the AC point.

* * * * *